US012648875B2

(12) United States Patent
Liu et al.

(10) Patent No.: US 12,648,875 B2
(45) Date of Patent: Jun. 9, 2026

(54) INTRAOCULAR IMPLANT DELIVERY DEVICE

(71) Applicant: HEALTH GUARD (SUZHOU) BIOMED. TECHNOLOGY CO., LTD, Suzhou (CN)

(72) Inventors: Hua Liu, Suzhou (CN); Zhongpeng Fan, Suzhou (CN)

(73) Assignee: HEALTH GUARD (SUZHOU) BIOMED. TECHNOLOGY CO., LTD, Suzhou (CN)

( * ) Notice: Subject to any disclaimer, the term of this patent is extended or adjusted under 35 U.S.C. 154(b) by 90 days.

(21) Appl. No.: 18/963,546

(22) Filed: Nov. 28, 2024

(65) Prior Publication Data

US 2025/0090374 A1      Mar. 20, 2025

Related U.S. Application Data

(63) Continuation of application No. PCT/CN2023/075737, filed on Feb. 13, 2023.

(30) Foreign Application Priority Data

May 30, 2022    (CN) .......................... 202210601358.4

(51) Int. Cl.
*A61F 9/007* (2006.01)
*A61F 9/00* (2006.01)
(52) U.S. Cl.
CPC ........ *A61F 9/00781* (2013.01); *A61F 9/0017* (2013.01)
(58) Field of Classification Search
CPC ........................... A61F 9/00781; A61F 9/0017
See application file for complete search history.

(56) References Cited

U.S. PATENT DOCUMENTS 7,090,681 B2 *   8/2006   Weber ............... A61M 37/0069
                                                         623/6.11
7,753,916 B2 *   7/2010   Weber .................... A61F 2/167
                                                         606/107
(Continued)

FOREIGN PATENT DOCUMENTS

CN          1681457 A  *  10/2005   ........... A61F 9/0017
CN       212214004 U      12/2020
(Continued)

OTHER PUBLICATIONS

The International search report for PCT Application No. PCT/CN2023/075737, dated May 15, 2023, 6 pages.
(Continued)

*Primary Examiner* — Guy K Townsend
(74) *Attorney, Agent, or Firm* — East IP P.C.

(57) ABSTRACT

Provided is an intraocular implant delivery device, comprising a housing, a main control pull rod assembly, a slider assembly a striking assembly, a retracting needle turntable, and a push needle assembly. The main control pull rod assembly, the slider assembly, the striking assembly, and the retracting needle turntable are all arranged in the housing. A through hole is provided at a distal end of the housing, and a push needle of the push needle assembly passes through the through hole and extends to an outer side of the housing. The main control pull rod assembly, the slider assembly, and the striking assembly are each provided with an energy source capable of selectively releasing energy. The main control pull rod assembly is actuated by an operator through a button arranged on the housing, so that the energy source drives the main control pull rod assembly to move axially.

12 Claims, 11 Drawing Sheets

(56)                References Cited

U.S. PATENT DOCUMENTS

| | | | | |
|---|---|---|---|---|
| 9,173,775 | B2 * | 11/2015 | Haffner | A61F 2/148 |
| 11,504,270 | B1 * | 11/2022 | Badawi | A61F 9/0008 |
| 2004/0054374 | A1 * | 3/2004 | Weber | A61B 17/3468 |
| | | | | 606/107 |
| 2004/0215133 | A1 * | 10/2004 | Weber | A61B 17/3468 |
| | | | | 604/60 |
| 2005/0101967 | A1 * | 5/2005 | Weber | A61F 9/0017 |
| | | | | 606/107 |
| 2005/0154399 | A1 * | 7/2005 | Weber | A61F 9/0017 |
| | | | | 606/107 |
| 2006/0241650 | A1 * | 10/2006 | Weber | A61F 2/167 |
| | | | | 606/107 |
| 2007/0293873 | A1 * | 12/2007 | Chang | A61K 9/0051 |
| | | | | 606/107 |
| 2009/0264813 | A1 * | 10/2009 | Chang | A61K 9/1647 |
| | | | | 604/60 |
| 2010/0241060 | A1 * | 9/2010 | Roizman | A61F 9/0017 |
| | | | | 604/257 |
| 2013/0253528 | A1 * | 9/2013 | Haffner | A61F 9/00781 |
| | | | | 606/107 |
| 2014/0213958 | A1 * | 7/2014 | Clauson | A61F 9/00781 |
| | | | | 604/8 |
| 2015/0065940 | A1 * | 3/2015 | Rangel-Friedman | |
| | | | | A61F 9/00781 |
| | | | | 604/8 |
| 2015/0133946 | A1 * | 5/2015 | Horvath | A61F 9/0017 |
| | | | | 606/108 |
| 2015/0238687 | A1 * | 8/2015 | Novakovic | A61F 9/0017 |
| | | | | 604/502 |
| 2016/0287438 | A1 * | 10/2016 | Badawi | A61K 33/14 |
| 2016/0354244 | A1 * | 12/2016 | Horvath | A61F 9/00736 |
| 2017/0273777 | A1 * | 9/2017 | Auld | A61F 2/1678 |
| 2019/0105077 | A1 * | 4/2019 | Kalina, Jr. | A61B 17/3468 |
| 2023/0301832 | A1 * | 9/2023 | Mansour | A61F 9/0017 |
| 2024/0024159 | A1 * | 1/2024 | Robinson | A61K 47/38 |

FOREIGN PATENT DOCUMENTS

| | | | |
|---|---|---|---|
| CN | 113058134 | A | 7/2021 |
| CN | 113509301 | A | 10/2021 |
| CN | 214805706 | U | 11/2021 |
| CN | 114983670 | A | 9/2022 |
| WO | 2015130945 | A1 | 9/2015 |
| WO | 2017087713 | A1 | 5/2017 |
| WO | 2019118901 | A2 | 6/2019 |

OTHER PUBLICATIONS

The First Office Action dated Feb. 26, 2025 for Chinese Application No. 202210601358.4 , 9 pages.
The First Office Action dated May 29, 2025 for RU Application No. 2024135975 , 11 pages.
The extended European search report dated Apr. 16, 2025 for European Application No. 23814650.0, 7 pages.

* cited by examiner

614

62

B-B

82

81

8

INTRAOCULAR IMPLANT DELIVERY DEVICE

CROSS-REFERENCE TO RELATED APPLICATION

The present application is a continuation of International Application No. PCT/CN2023/075737 filed on Feb. 13, 2023, which claims priority to Chinese Patent Application No. 202210601358.4, entitled "INTRAOCULAR IMPLANT DELIVERY DEVICE", filed on May 30, 2022, both of which are incorporated herein by reference in their entireties.

TECHNICAL FIELD

The present application relates to the technical field of medical instruments, in particular to an intraocular implant delivery device.

BACKGROUND

Glaucoma is a group of diseases that are commonly characterized by optic nerve atrophy and depression, visual field loss and decreased vision. Glaucoma is associated with increased intraocular pressure, usually due to the inability of the ocular drainage channels to adequately remove aqueous humor from the anterior chamber of the eye, or due to excessive aqueous humor production caused by the ciliary body in the eye. Patients often experience symptoms such as nausea and pain, if not treated in time, it will lead to vision loss. For the treatment of glaucoma, surgical filtration methods can be used to reduce intraocular pressure by creating a fluid flow path between the anterior chamber and the low-pressure area. Ocular implants can be positioned in the eye to drain fluid from the anterior chamber to multiple locations, such as the sub-Tenon's space, subconjunctival space, suprascleral vein, suprachoroidal space, Schlemm canal, and intrascleral space. Ocular implants are generally often prepared from a selection of animal-derived/non-animal-derived polymers, metals, and other materials, and are generally prevalent in tubular or tubelike form. According to the different mechanisms of reducing intraocular pressure in glaucoma, drainage of aqueous humor through the subconjunctival space and the superior scleral vein is more effective. The common surgical pathways are to penetrate the atrial angle area through the anterior chamber from a microcorneal incision, reach the subconjunctival space through the sclera, or reach the suprachoroidal space through the anterior chamber angle. This type of operation requires a corresponding delivery mechanism to deliver the implant to the corresponding part of the eye.

One type of MIGS surgery involves implanting an intraocular implant such as a stent into a trabecular meshwork to create an aqueous humor outflow pathway and reduce intraocular pressure. A typical implantation method is to make a corneal incision and insert the implant into a desired implantation site using a delivery device with a puncture needle. It is known that U.S. Pat. No. 9,173,775B2 discloses a system for delivering a plurality of ocular implants. The system is actuated by means of a cam and a torsion spring and can sequentially push the plurality of implants to desired sites in the eye, where the torsion spring is an energy source for the structural design, which attenuates after one implant is pushed each time. The energy for pushing the second implant is significantly less than that for pushing the first implant. Therefore, the number of implants that can be pushed by the structure is limited, typically only two. To achieve accurate delivery of an implant in the present application, the distance between the distal end of a push needle retracted each time and the tail of the implant should be constant. The size of the implant is very small, only within 0.5 mm, and even small deviations can affect the accuracy of delivery. Therefore, the requirements for the manufacturing process are very high. The cam design in existing technologies requires drilling a hole on half of a housing, such as on a left housing during assembly. The left housing is first fixed to a centering pin through the hole, then the cam passes through the centering pin and is fixed, and other components are assembled. Because a gap needs to be reserved for hole-shaft fit, when a right housing is assembled with the left housing, the hole-shaft fit of the cam may lead to axial swing, and the front end of a push needle assembly is misaligned to affect the accuracy of grasping the implant by the front end of the push needle, resulting in defects such as empty launch or launch of two implants at a single time.

SUMMARY

One of the objectives of the present application is to provide an intraocular implant delivery device that can solve the aforementioned problems in the background that the energy for subsequently pushing another implant is insufficient and implants cannot be pushed multiple times because the energy of a torsion spring attenuates after the existing intraocular implant delivery device pushes one implant each time, and empty launch or launch of two implants at a single time may occur because the swing caused by the hole-shaft fit of a cam affects the reliability of grasping the implant by the front end of a push needle of the delivery device in the manufacturing process.

To achieve the above objective, embodiments of the present application provide the following technical solution:

an intraocular implant delivery device including a housing, a main control pull rod assembly, a slider assembly, a striking assembly, a retracting needle turntable, and a push needle assembly, the main control pull rod assembly, the slider assembly, the striking assembly, and the retracting needle turntable being arranged in the housing, a through hole being provided at a distal end of the housing, a push needle of the push needle assembly extending through the through hole to an outer side of the housing, and the main control pull rod assembly, the slider assembly, and the striking assembly are each provided with an energy source capable of selectively releasing energy;

the main control pull rod assembly is actuated by an operator through a button arranged on the housing, so that the energy source drives the main control pull rod assembly to move axially;

the slider assembly is longitudinally adjacent to a main control pull rod, and several protrusions are provided on the side surface of the main control pull rod facing the slider assembly; when the button is pressed and the main control pull rod moves axially, the protrusions can push the slider assembly to move longitudinally away from the button; when the protrusions move away from the slider assembly with the main control pull rod, the energy source pushes the slider assembly to move longitudinally close to the button to an initial position;

the retracting needle turntable is arranged on a distal side of the slider assembly, several limit steps are provided on the side surface of the retracting needle turntable facing the push needle assembly, and a driving member for driving the retracting needle turntable to rotate is provided on the slider assembly; when the slider assembly moves longitudinally away from the button, the driving member drives the retracting needle turntable to rotate an angle corresponding to one step, so that the push needle of the push needle assembly retracts one step towards a proximal end;

the striking assembly is arranged on a proximal side of the slider assembly; when the slider assembly is in the initial position, the energy source connected to the striking assembly is in an energy storage state; when the slider assembly moves longitudinally away from the button, the striking assembly moves along a guide curved surface of the slider assembly towards the distal end under the push of the energy source to strike the push needle assembly; and the push needle assembly is arranged on a distal side of the retracting needle turntable, at least one implant is accommodated inside the push needle, and an elastic claw is provided at a distal end of the push needle; when the push needle retracts towards the proximal end, the elastic claw opens when passing through the implant, so that the elastic claw moves from a head of the implant to a tail of the implant; when the striking assembly strikes the push needle assembly, the push needle assembly drives the push needle to move towards the distal end of the housing, to push the implant to an implantation site of a patient.

As a further optimization of the above solution, the energy source is a spring, motor, magnetic iron or elastomer.

As a further optimization of the above solution, the main control pull rod assembly includes a main control pull rod and a spring, the spring is the energy source connected to the main control pull rod, one end of the spring is fixed to the main control pull rod and the other end is fixed to the housing; when the button is in the initial position, the button limits the main control pull rod, and the spring is in the energy storage state; when the button is pressed, the spring pushes the main control pull rod to move axially towards the proximal or distal end.

As a further optimization of the above solution, a plurality of groups of first limit blocks and second limit blocks are provided on the side surface of the main control pull rod away from the slider assembly, and the first limit blocks and the second limit blocks are alternately arranged and used to limit the main control pull rod when the button is pressed and released; a width of the protrusion corresponds to a distance between the adjacent first limit blocks.

As a further optimization of the above solution, the button actuates the main control pull rod through a lever and a reset spring, a shaft hole is provided at a middle part of the lever, a fixing shaft is provided inside the housing, the fixing shaft passes through the shaft hole on the lever, one end of the lever corresponds to the position of the button, the other end of the lever is connected to the reset spring, a positioning block is provided on the lever, and the positioning block is used for limiting the main control pull rod.

As a further optimization of the above solution, the slider assembly includes a slider and a spring, the spring is the energy source connected to the slider, the slider includes a side plate and two guide plates extending vertically outward from the side plate, the two guide plates are spaced apart, the guide curved surface is provided on opposite surfaces of the two guide plates respectively, the through hole corresponding to the striking assembly is provided on the side plate between the two guide plates, and the driving member is arranged on the side plate of the slider.

As a further optimization of the above solution, a component magnetically coupled with the driving member is provided on the retracting needle turntable; when the slider assembly moves longitudinally away from the button, the driving member pushes the retracting needle turntable to rotate an angle corresponding to one step under the action of magnetic force, so that the push needle of the push needle assembly retracts one step axially towards the proximal end.

As a further optimization of the above solution, the driving member is an elastic plectrum, several plectrum blocks are provided on the retracting needle turntable, and the plectrum blocks are distributed on the retracting needle turntable at a set circumferential spacing; when the slider assembly moves longitudinally away from the button, the elastic plectrum on the slider assembly pushes the plectrum blocks to move, the retracting needle turntable is driven to rotate an angle corresponding to one step, and the push needle of the push needle assembly retracts one step axially towards the proximal end.

As a further optimization of the above solution, the striking assembly includes a striking head and a spring limit portion, a spring is provided between the spring limit portion and the housing, and a guide limit block is provided on the striking head; when the slider assembly slides longitudinally away from the button, the guide limit block slides along the guide curved surface, so that the striking head moves towards the distal end to strike the push needle assembly; when the slider assembly slides longitudinally close to the button, the guide curved surface pushes the striking head to move towards the proximal end, and the third spring stores energy.

As a further optimization of the above solution, a guide strip is provided at a lower part of the spring limit portion, a corresponding axial guide groove is provided inside the housing, and the guide strip is in sliding fit with the axial guide groove.

As a further optimization of the above solution, the push needle assembly includes the push needle, a push needle assembly seat, and a spring; the push needle is fixed on the push needle assembly seat, a gear wall for fixing the spring is provided on the housing, the spring is sleeved on the push needle and connected between the push needle assembly seat and the gear wall, and the push needle assembly seat abuts against the steps of the retracting needle turntable, so that when the retracting needle turntable rotates, the spring pushes the push needle assembly seat to move axially towards the proximal end, to drive the push needle to move from the head of the implant to the tail of the implant; the striking assembly strikes the push needle assembly seat when moving towards the distal end, to push the push needle to strike the implant.

As a further optimization of the above solution, the intraocular implant delivery device further includes a puncture needle assembly for forming an incision in an ocular tissue; a slide knob is further provided on the housing to control the puncture needle assembly to retract towards the proximal end.

It should be noted that the expressions of the directions such as up, down, left, right, front, and rear mentioned in the above solution are only for the convenience of understanding the solution of the present application, and are not intended to limit the scope of protection of the present application. When the placement direction of the intraocular implant delivery device is different, these directions will have synchronous rotational changes. The directions in the above solution are described based on the direction in which the operator holds the intraocular implant of the present application during surgery. The distal end refers to a direction away from the operator or towards an eye tissue, while the proximal end refers to a direction towards the operator or away from the eye tissue.

The embodiments of the present application have at least some of the following beneficial effects:

1) The intraocular implant delivery device according to the embodiments of the present application mainly achieves an implantation operation of intraocular implants through the main control pull rod assembly, the slider assembly, the striking assembly, and the push needle assembly. According to the needs of an implantation surgery, implants can be repeatedly delivered to the patient's trabecular meshwork, thereby improving the efficiency of the implantation surgery. Only one puncture is required to complete the implantation surgery, which can improve the implantation precision of the implants.

2) The intraocular implant delivery device according to the embodiments of the present application utilizes the energy source connected to the main control pull rod as a total energy source, and the main control pull rod sequentially and constantly configures the total energy source to the slider assembly and the striking assembly that need to be driven, thereby ensuring that the striking assembly can deliver constant energy to an implant each time. Compared with the solution in existing technologies that the delivery energy gradually attenuates, the present application can ensure that implants can be delivered multiple times according to surgical needs and extremely high precision each time the implant is delivered can be achieved.

3) According to the intraocular implant delivery device according to the embodiments of the present application, the retracting needle turntable controls the retracting needle distance of the push needle assembly to ensure that the retracting needle distance of each push is just adapted to the size of an implant, so that the elastic claw at the distal end of the push needle can accurately move to the tail of a to-be-delivered implant each time. The high-precision retracting needle design can effectively overcome the problem of empty launch of an implant or launch of two implants at a single time due to low grasping precision of the push needle in the existing technologies, thereby further improving the precision and safety of the intraocular implant surgery.

4) In the embodiments of the present application, the axial movement of the main control pull rod drives the longitudinal movement of the slider assembly, which in turn drives the axial movement of the striking assembly. These movements are all straight movements, which can further improve and ensure the precision and reliability of implant delivery.

5) When the intraocular implant delivery device according to the embodiments of the present application delivers intraocular implant, one implant can be implanted by pressing the button once, with simple operation and high reliability.

6

Figure 3:
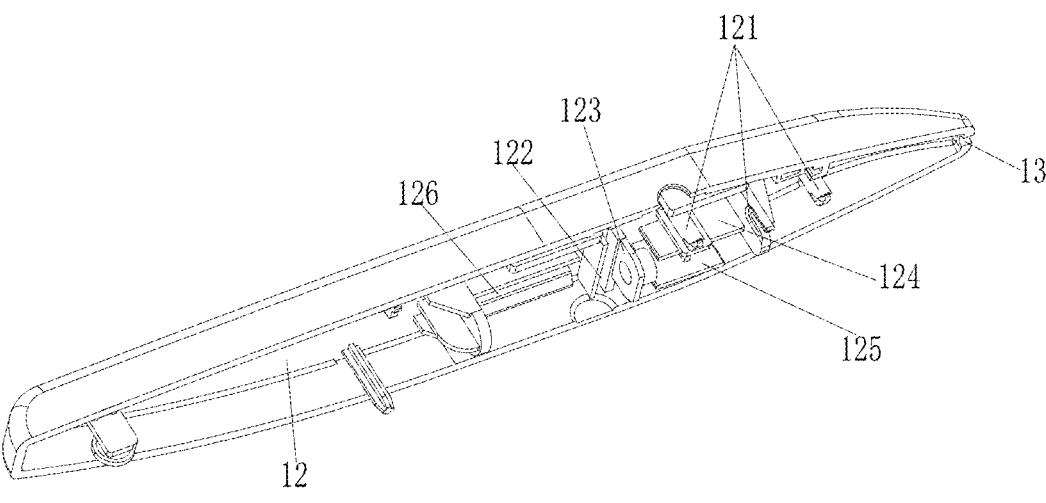

FIG. 3 is a schematic structural view of a left housing of the intraocular implant delivery device in Embodiment 1 of the present application.

Figure 4:
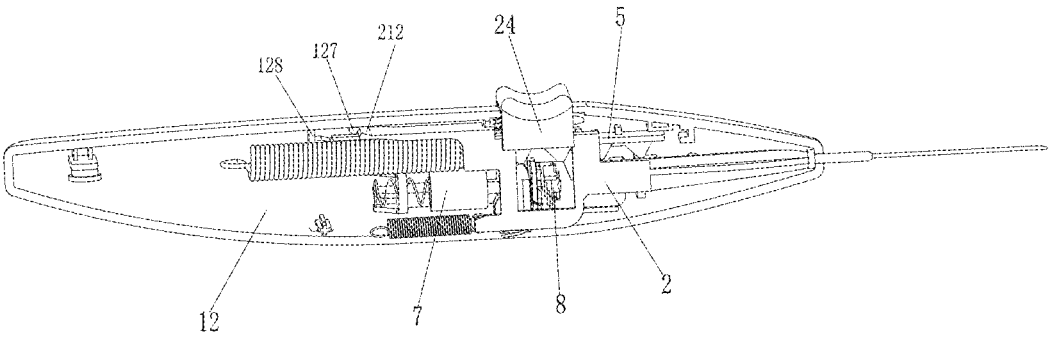

FIG. 4 is a schematic view of an internal structure of the intraocular implant delivery device in Embodiment 1 of the present application.

Figure 5:
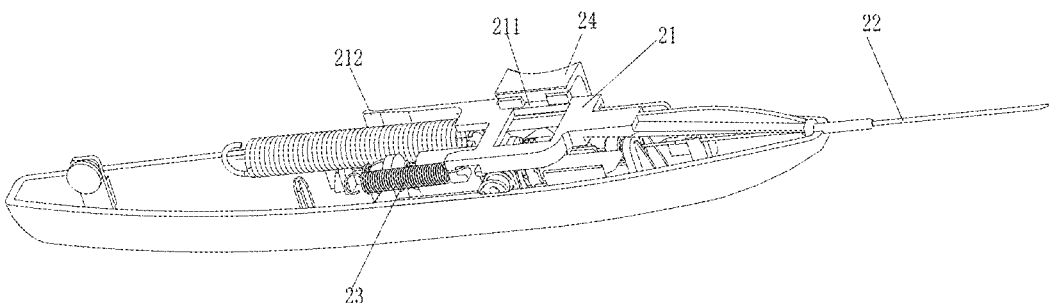

FIG. 5 is a schematic view (top view) of the internal structure of the intraocular implant delivery device in Embodiment 1 of the present application.

Figures 6, 7:
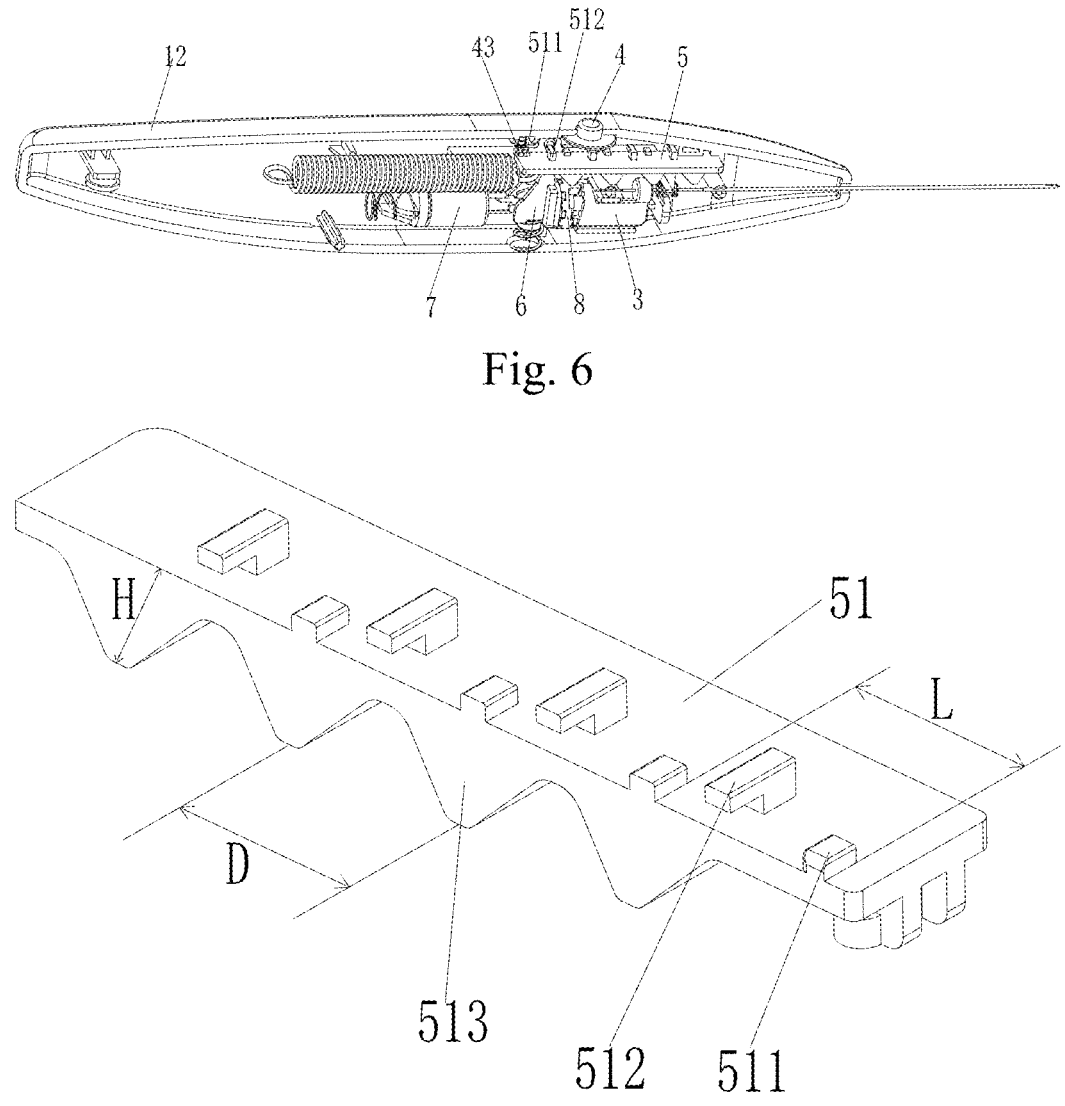

FIG. 6 is a schematic view of the internal structure of the intraocular implant delivery device in Embodiment 1 of the present application (without a puncture needle assembly).

FIG. 7 is a schematic structural view of a main control pull rod.

Figure 8:
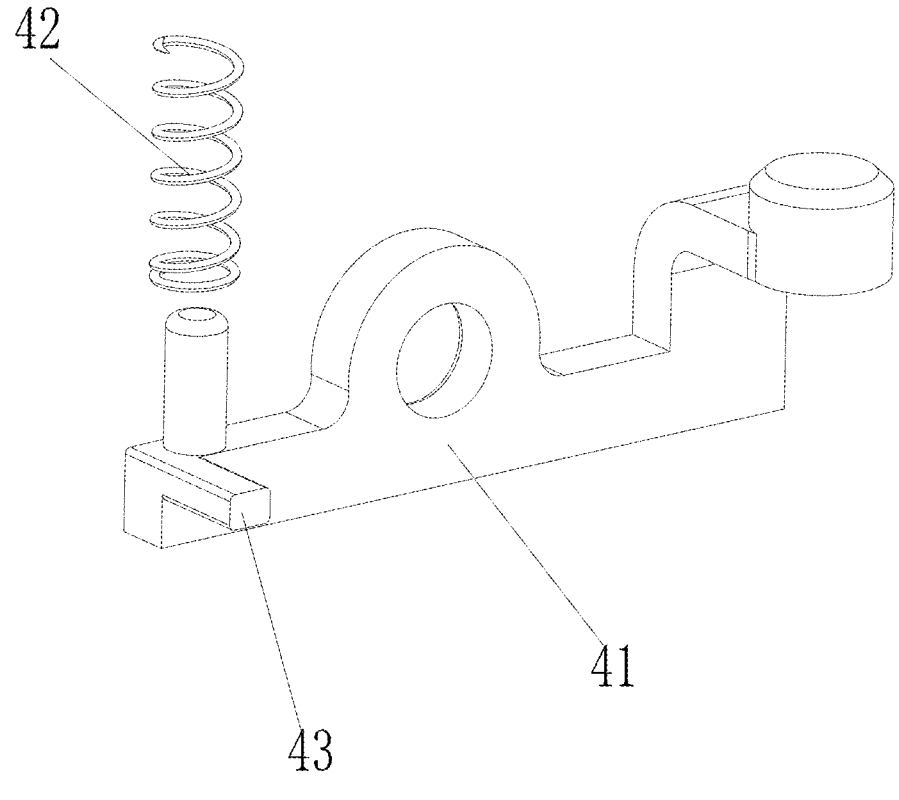

FIG. 8 is a schematic structural view of a lever.

Figure 9:
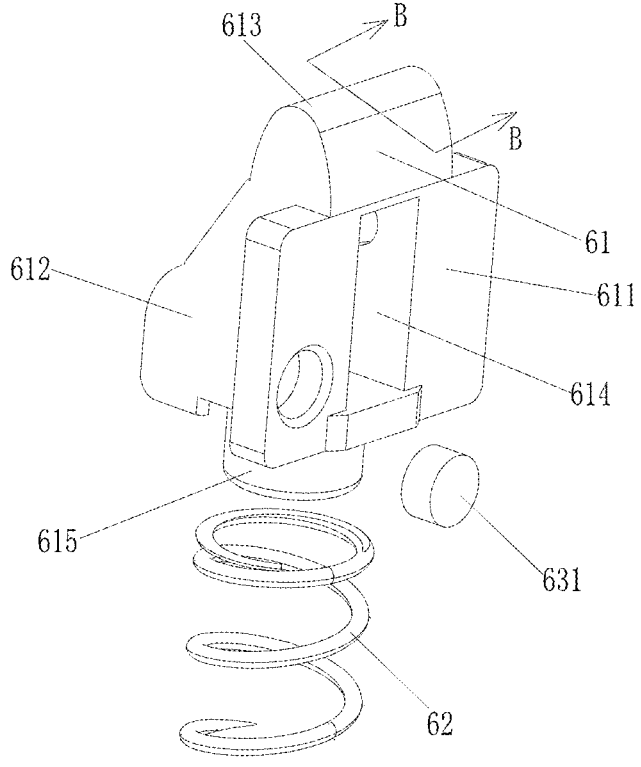

FIG. 9 is a schematic structural view of a slider assembly in Embodiment 1.

Figure 10:
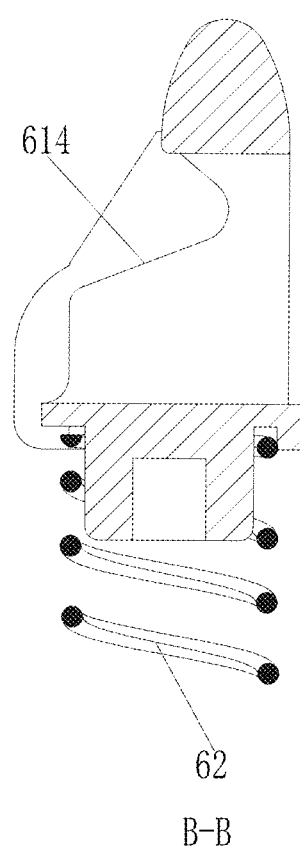

FIG. 10 is a cross-sectional view of a slider taken in a B-B direction.

Figure 11:
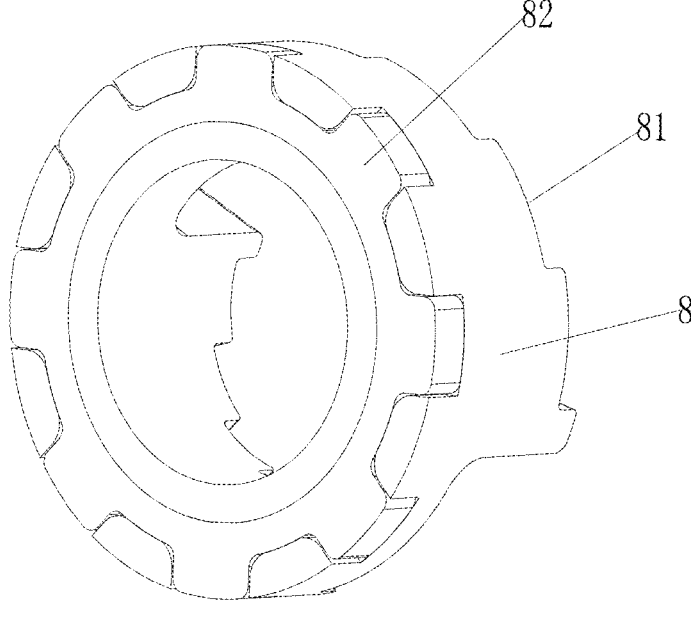
Figure 12:
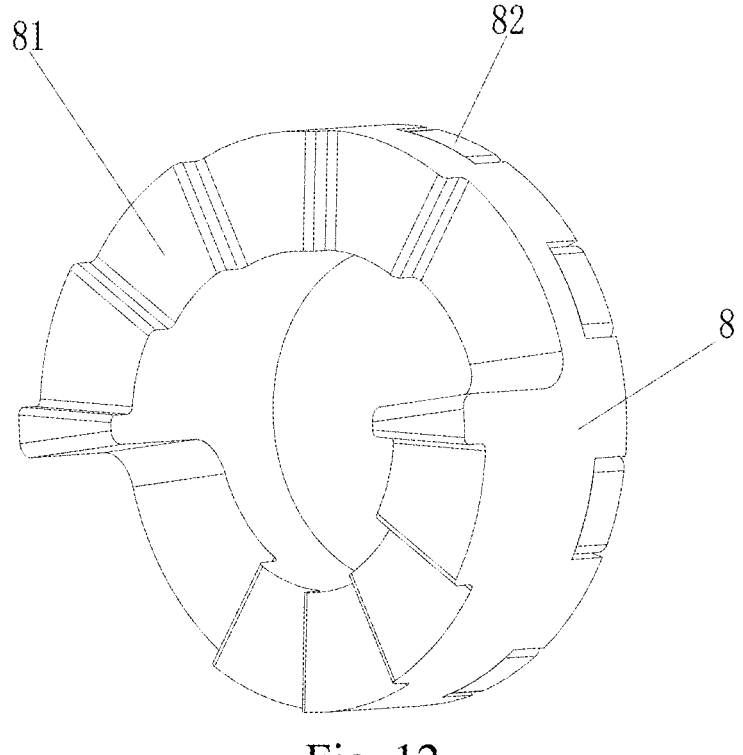
Figure 13:
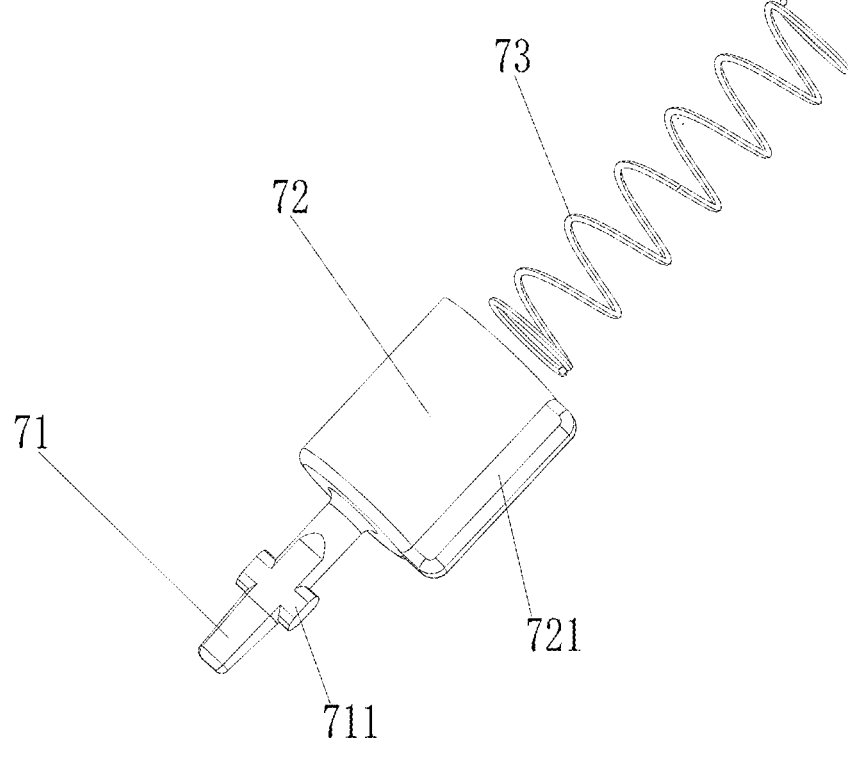

FIG. 11 is a schematic structural view of a retracting needle turntable (viewed from a distal end);

FIG. 12 is a schematic structural view of the retracting needle turntable (viewed from a proximal end);

FIG. 13 is a schematic structural view of a striking assembly.

Figure 14:
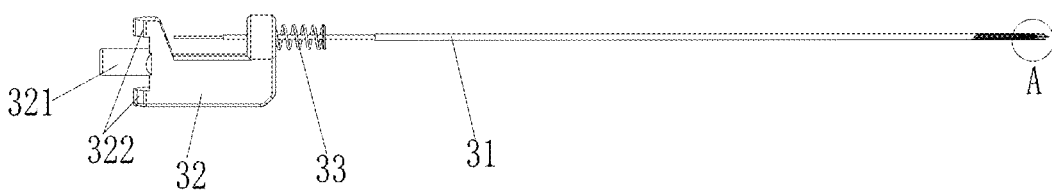

FIG. 14 is a schematic structural view of a push needle assembly.

Figure 15:
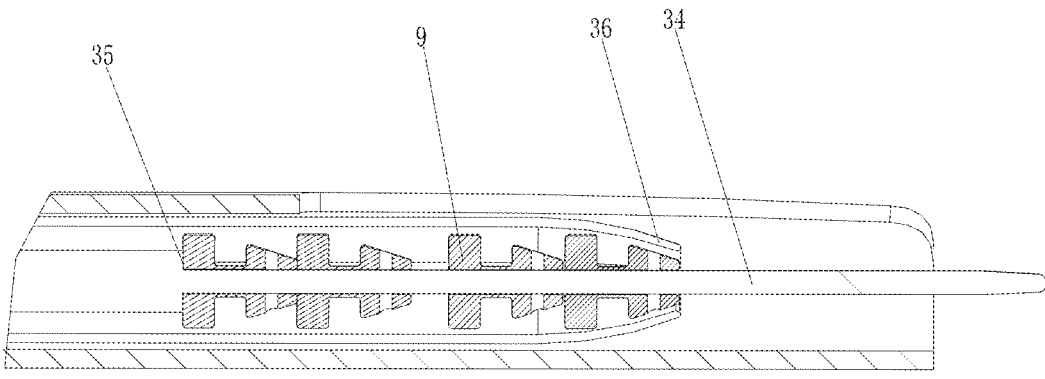

FIG. 15 is a partially enlarged view of part A of the push needle assembly.

Figure 16:
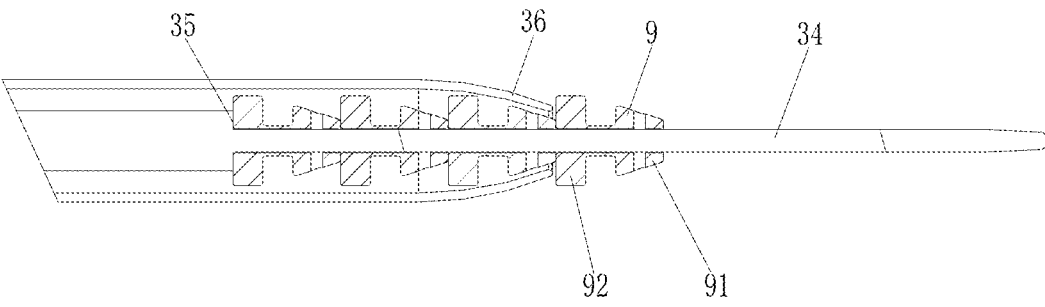

FIG. 16 is a schematic structural view of an elastic claw of the push needle retracted from a head to a tail of an implant.

Figure 17:
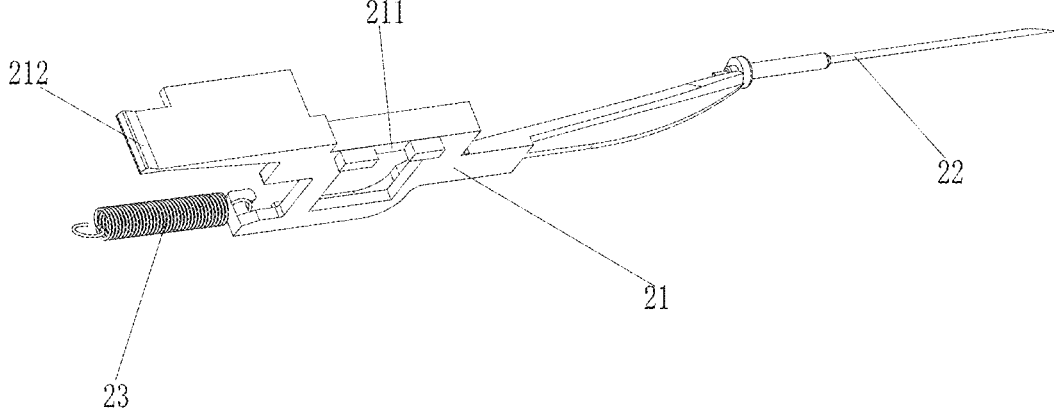

FIG. 17 is a schematic structural view of a puncture needle assembly.

Figure 18:
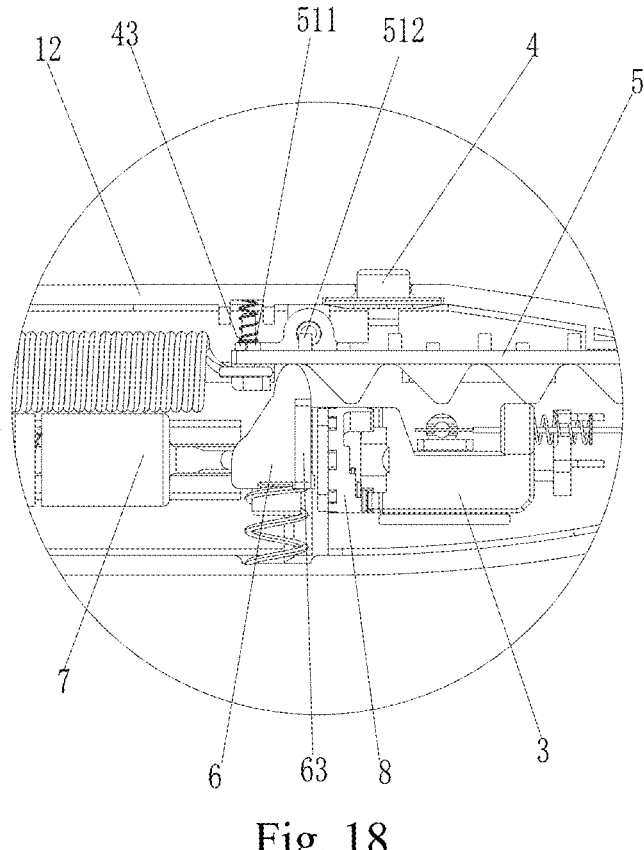

FIG. 18 is a partially enlarged internal cross-sectional view of the intraocular implant delivery device in Embodiment 1 when a button is in an initial state.

Figure 19:
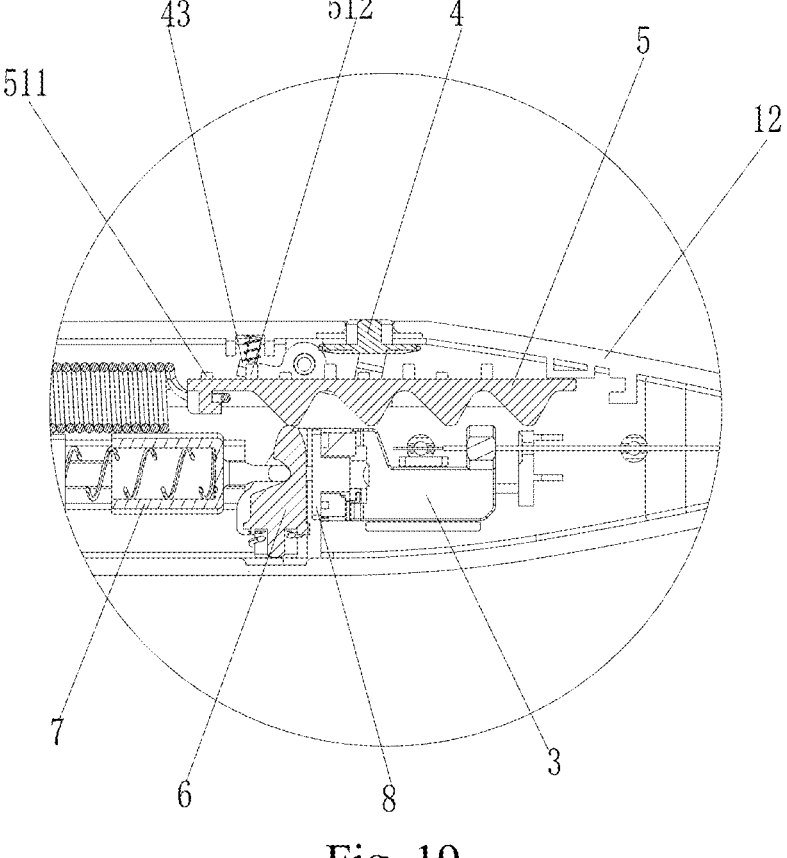

FIG. 19 is a partially enlarged internal cross-sectional view of the intraocular implant delivery device in Embodiment 1 when the button is pressed.

Figure 20:
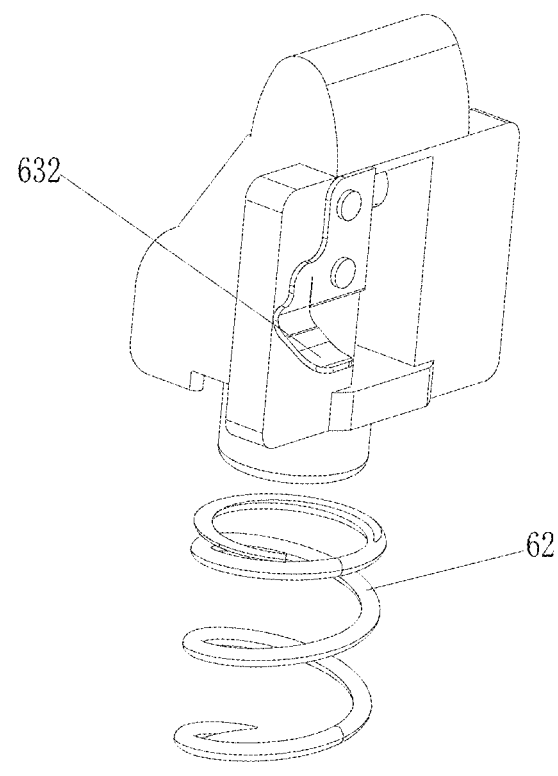

FIG. 20 is a schematic structural view of a slider assembly in Embodiment 2.

Figure 21:
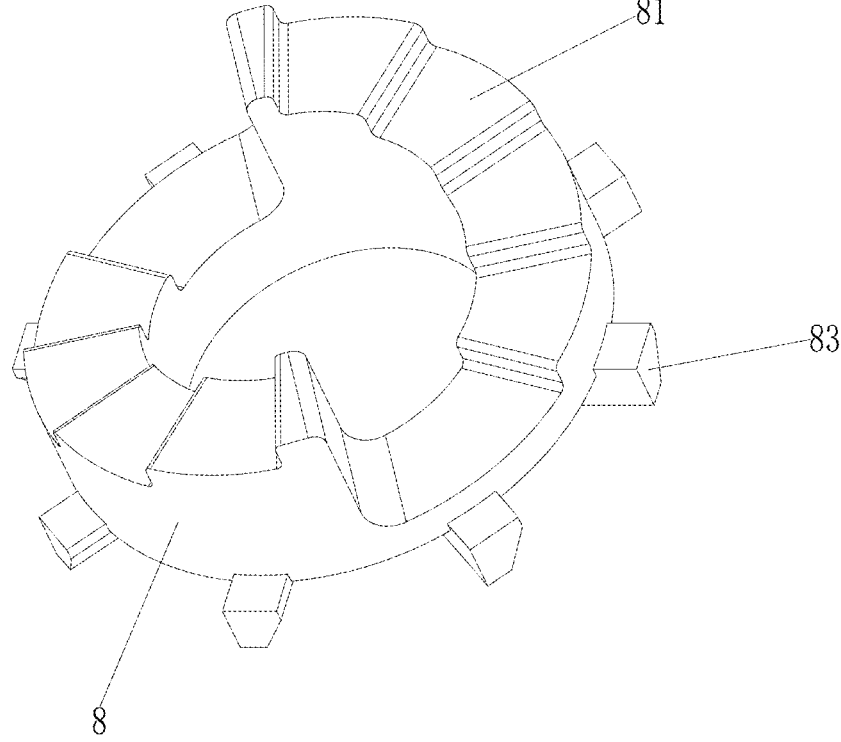

FIG. 21 is a schematic structural view of a retracting needle turntable in Embodiment 2.

LIST OF REFERENCES housing 1, right housing 11, left housing 12, push needle guide limit member 121, chute 122, retracting needle turntable assembly seat 123, front guide limit plate 124, rear guide limit plate 125, axial guide groove 126, first limit rib 127, second limit rib 128, through hole 13; puncture needle assembly 2, puncture needle assembly seat 21, limit groove 211, elastic limit portion 212, puncture needle 22, tension spring 23, slide knob 24; push needle assembly 3, push needle 31, push needle assembly seat 32, striking portion 321, limit portion 322, compression spring 33, implant positioning rod 34, limit portion 35, elastic claw 36, button 4, lever 41, reset spring 42, positioning block 43, main control pull rod assembly 5, main control pull rod 51, first limit block 511, second limit block 512, protrusion 513, slider assembly 6, slider 61, side plate 611, guide plate 612, guide curved surface 613, through hole 614, spring positioning portion 615, compression spring 62, driving member 63, magnetic block 631, elastic plectrum 632, striking assembly 7, striking head 71, guide limit block 711, spring limit portion 72, guide strip 721, energy source 73, retracting needle turntable 8, limit step 81, iron ring 82, plectrum block 83, implant 9.

DETAILED DESCRIPTION

The technical solutions of the present application will be clearly and completely described below through embodiments. Apparently, the described embodiments are only some of the embodiments of the present application, not all of them. Based on the embodiments in the present application, all other embodiments obtained by those of ordinary skill in the art without any creative effort shall fall within the scope of protection of the present application.

In the description of the present application, it should be understood that the orientation or positional relationship related to orientation description, such as up, down, front, rear, left, and right, is based on the orientation or positional relationship shown in the accompanying drawings, is only for the convenience of describing the embodiments of the present application and simplifying the description, does not indicate or imply that the apparatus or component referred to must have a specific orientation or be constructed and operated in a specific orientation, and therefore cannot be understood as a limitation on the embodiments of the present application.

In the description of the embodiments of the present application, "several" means one or more; "a plurality of" means two or more; "greater than", "less than", "more than", etc. are understood as not including that number; and "above", "below", "within", etc. are understood as including that number. Described "first" and "second" are only for distinguishing technical features, and cannot be understood as indicating or implying the relative importance or implicitly indicating the quantity of the indicated technical features or implicitly indicating the sequence of the indicated technical features.

In the description of the embodiments of the present application, unless otherwise explicitly limited, the terms such as "arrange", "mount", and "connect" should be understood in a broad sense. Those skilled in the art can reasonably determine the specific meanings of the above terms in the present application in conjunction with the specific content of the technical solution.

It should be noted that the embodiments in the present application and the features in the embodiments can be combined with each other on a non-conflict basis. The following will provide a detailed description of the embodiments in conjunction with the accompanying drawings.

In each embodiment of the present application, the distal end refers to a direction away from an operator or towards an eye tissue, while the proximal end refers to a direction towards the operator or away from the eye tissue.

The following provides an overall explanation of the embodiments of the present application.

An intraocular implant delivery device according to embodiments of the present application includes a housing 1, a main control pull rod assembly 5, a slider assembly 6, a striking assembly 7, a retracting needle turntable 8, and a push needle assembly 3. The main control pull rod assembly 5, the slider assembly 6, the striking assembly 7, and the retracting needle turntable 8 are all arranged in the housing 1. A through hole 13 is provided at a proximal end of the housing 1, and a push needle 31 of the push needle assembly 3 passes through the through hole 13 and extends to an outer side of the housing 1. The main control pull rod assembly 5, the slider assembly 6, and the striking assembly 7 are each provided with an energy source 73 capable of selectively releasing energy.

The main control pull rod assembly 5 is actuated by an operator through a button 4 arranged on the housing 1, so that the energy source 73 drives the main control pull rod assembly 5 to move axially.

The slider assembly 6 is longitudinally adjacent to a main control pull rod 51, and several protrusions 513 are provided on the side surface of the main control pull rod 51 facing the slider assembly 6. When the button is pressed and the main control pull rod 51 moves axially, the protrusions 513 can push the slider assembly 6 to move longitudinally away from the button 4. When the protrusions 513 move away from a slider 61 with the main control pull rod 51, the energy source 73 pushes the slider assembly 6 to move longitudinally close to the button 4 to an initial position.

The retracting needle turntable 8 is arranged on a distal side of the slider assembly 6, several limit steps 81 are provided on the side surface of the retracting needle turntable 8 facing the push needle assembly 3, and a driving member 63 for driving the retracting needle turntable 8 to rotate is provided on the slider assembly 6. When the slider assembly 6 moves longitudinally away from the button, the driving member 63 drives the retracting needle turntable 8 to rotate an angle corresponding to one step, so that the push needle 31 of the push needle assembly 3 retracts one step towards the proximal end.

The striking assembly 7 is arranged on a proximal side of the slider assembly 6. When the slider assembly 6 is in the initial position, the energy source 73 connected to the striking assembly 7 is in an energy storage state. When the slider assembly 6 moves longitudinally away from the button, the striking assembly 7 moves along a guide curved surface 613 of the slider assembly 6 towards the distal end under the push of the energy source 73 to strike the push needle assembly 3.

The push needle assembly 3 is arranged on a distal side of the retracting needle turntable 8, at least one implant 9 is accommodated inside the push needle 31, and an elastic claw 36 is provided at a distal end of the push needle 31. When the push needle 31 retracts towards the proximal end, the elastic claw 36 opens when passing through the implant 9, so that the elastic claw 36 moves from a head of the implant 9 to a tail of the implant. When the striking assembly 7 strikes the push needle assembly 3, the push needle assembly 3 drives the push needle 31 to move towards the distal end of the housing 1, to push the implant 9 to an implantation site of a patient.

Specifically, the energy source 73 capable of selectively releasing energy in the embodiments of the present application indicates that the energy source 73 can store energy or release energy according to different working states. The energy source 73 may be a spring, motor, magnetic iron or elastomer.

More specifically, in one embodiment, springs are used as mechanisms for storing and releasing energy, where a first spring is connected to the main control pull rod 51, a second spring is connected to the slider assembly 6, and a third spring is connected to the striking assembly 7. The first spring may be a tension spring or a compression spring, the second spring may be a tension spring or a compression spring, and the third spring may be a tension spring or a compression spring, depending on the actual layout in the housing 1 to select. Further, whether the main control pull rod assembly 5 moves towards a distal or proximal end in an axial direction depends on whether the first spring is a tension spring and the position of the first spring. For example, if the first spring is a tension spring and is located on a proximal side of the main control pull rod, the main control pull rod assembly moves towards the proximal end in the axial direction. The axial direction is parallel to the axial direction of the push needle.

From the perspective of the operator holding the intraocular implant delivery device, the button 4 is located at an upper part of housing 1, and the slider assembly 6 is located below the main control pull rod assembly 5; the striking assembly 7, the slider assembly 6, the retracting needle turntable 8, and the push needle assembly 3 are arranged in sequence from right to left in the axial direction; the longitudinal upward movement of the slider assembly 6 is towards the direction close to the button 4, while the longitudinal downward movement of the slider assembly 6 is towards the direction away from the button. In another embodiment, if the button 4 is located at a lower part of housing 1, the slider assembly 6 is located above the main control pull rod assembly 6; the striking assembly 7, the slider assembly 6, the retracting needle turntable 8, and the push needle assembly 3 are arranged in sequence from right to left in the axial direction; the slider assembly 6 moves upward longitudinally when the button 4 is pressed, the slider assembly 6 moves downward longitudinally when the button 4 is reset, the longitudinal upward movement of the slider assembly 6 is towards the direction away from the button, and the longitudinal downward movement of the slider assembly 6 is towards the direction close to the button 4.

The main control pull rod 51 is activated by the button 4. When the button 4 is pressed, the main control pull rod 51 moves straight axially under the action of the first spring. The protrusions 513 are provided on the side surface of the main control pull rod 51 facing the slider assembly 6, the protrusions 513 push the slider assembly 6 to move straight downward longitudinally, and the protrusions 513 have certain designed contour surfaces, which may be triangular, semi-circular, semi-elliptic, arc-shaped, trapezoidal, etc.

Assuming the height of the protrusions 513 is h, when the slider assembly 6 moves downward along a trajectory of the protrusions 513, the driving member 63 on the slider assembly 6 is first utilized to cause the rotation of the retracting needle turntable 8, and the driving member 63 drives the retracting needle turntable 8 to rotate an angle corresponding to one step, that is, when the distance of downward movement of the slider assembly 6 is less than h, the retracting needle turntable 8 already rotates into place. Several limit steps 81 are provided on the side surface of the retracting needle turntable 8 facing the push needle assembly 3, and the limit steps 81 may be distributed along both sides of the entire circumference or along the single-sided circumference; the steps in one cycle are arranged in sequence from high to low, and the heights of adjacent steps, the width of each step, and the angle of rotation by one step are related to the retracting distance of the push needle 31 and the length of the implant 9.

In the initial position, the push needle assembly 3 abuts against the high step of the retracting needle turntable 8. When the slider assembly 6 moves downward, the retracting needle turntable 8 rotates, the push needle assembly 3 falls onto the low step to achieve retracting the push needle assembly 3 in the axial direction, the elastic claw 36 of the push needle 31 moves from the head of the implant 9 to the tail of the implant 9, and the elastic claw 36 abuts against the tail of the implant 9.

In the initial position, the third spring of the striking assembly 7 is in an energy storage state. When the slider assembly 6 moves downward, the striking assembly 7 moves along the guide curved surface 613 of the slider assembly 6 towards the distal end under the push of the third spring. As the slider assembly 6 continues to move downward to the distance h, the slider assembly 6 is located at the highest point of the protrusions 513, the striking assembly 7 is located at the farthest point in the axial direction and just contacts and strikes the push needle assembly 3, and the push needle assembly 3 drives the push needle 31 to move towards the distal end of the housing 1, to push the implant 9 to the implantation site of the patient.

The intraocular delivery of one implant is completed by the above process of first retracting and then striking, which is a continuous process. When the button 4 is released, the slider assembly 6 moves upward along the protrusions 513 to its initial state. When the slider assembly 6 moves upward, blocked by the high step of the retracting needle turntable 8, the retracting needle turntable 8 cannot rotate, and the push needle assembly 3 also does not move along the axis; and the striking assembly 7 moves along the guide curved surface 613 of the slider assembly 6 axially towards the proximal end and returns to its initial state, to prepare for the delivery of the next implant.

In the above process, the main control pull rod assembly 5 only moves straight axially and does not move up or down; the slider assembly 6 only moves straight longitudinally and does not move left or right; and the striking assembly 7 only moves straight axially and does not move up or down. Such limit and straight movement improve and ensure the accuracy and reliability of implant delivery. Specifically, the limit can be implemented by providing a limit mechanism on the housing 1, or by providing a corresponding guide bar and chute on a component and the housing, or by other additional mechanisms.

The implant in the embodiments of the present application may be an implant with a central through hole. The implant is delivered to the trabecular meshwork to create an aqueous humor outflow pathway between the anterior chamber and the Schlemm canal, thereby reducing the increased intraocular pressure. According to actual surgical needs, an incision is formed in the eye tissue, and the distal end of the push needle is placed at the trabecular meshwork. One, two, three, four, or more implants can be delivered.

The number of protrusions 513 and the number of limit steps 81 on the retracting needle turntable 8 are set according to the maximum number of implants 9. The first spring connected to the main control pull rod 51 is used as a total energy source 73, and the second spring and third spring are used as secondary energy sources 73. The attenuation of the total energy source 73 keeps the secondary energy sources 73 constant. If the total energy source 73 is large enough, it can be considered that an infinite number of implants can be implanted by the delivery device.

A plurality of implants 9 are accommodated inside the push needle 31, an elastic claw 36 is provided at the distal end of the push needle 31, and the elastic claw 36 retracts and advances to deliver the plurality of implants. The push needle 31 of the push needle assembly 3 is a hollow needle, an implant positioning rod 34 is provided inside the push needle 31, a limit portion 35 is provided on the implant positioning rod 34, and an elastic claw 36 is provided at the distal end of the push needle 31. The appropriate elastic claw 36 may be selected according to the shape of the implant; for example, at least two axial grooves may be provided at the distal end of the push needle to divide the distal end of the push needle into at least two parts, namely, at least two claws. The distal end of the push needle 31 is made of an elastic material. When the push needle retracts to the head of the implant, the elastic claw 36 automatically opens along the outer surface of the implant until the elastic claw moves to the tail of the implant, and then the elastic claw automatically closes under the action of elasticity. When a striking head of the striking assembly 7 strikes the push needle assembly 3, the push needle assembly 3 drives the push needle 31 to move towards the distal end of the housing 1, to push the implant 9 to the implantation site of the patient.

If the number of implants 9 is one, only one protrusion 513 can be provided on the main control pull rod assembly 5, the button 4 is arranged on the housing 1 and extends to the outside of the housing 1, and the button 4 can actuate and release the main control pull rod assembly 5 through a reset spring 42.

If the number of implants 9 is two or more, a plurality of groups of first limit blocks 511 and second limit blocks 512 can be provided on the side surface of the main control pull rod 51 away from the slider assembly 6, and the first limit blocks 511 and the second limit blocks 512 are alternately arranged and used to limit the main control pull rod 51 when the button 4 is pressed and released; the width of the protrusion 513 corresponds to the distance between the adjacent first limit blocks 511. Specifically, the button 4 can actuate the main control pull rod 51 through a lever 41 and the reset spring 42; a shaft hole is provided at a middle part of the lever 41, a fixing shaft is provided inside the housing 1 and passes through the shaft hole on the lever 41; one end of the lever 41 corresponds to the position of the button 4, the other end of the lever 41 is connected to the reset spring 42, a positioning block 43 is provided on the lever 41 to limit the main control pull rod 51.

An incision is formed in the eye tissue before surgery. After the incision is formed at the cornea by other surgical instruments, the push needle 31 of the delivery device in the present application is delivered to the trabecular meshwork; or after the incision is pre-formed, the puncture needle assembly 2 of the delivery device in the present application punctures the incision at the cornea and enters the trabecular meshwork. The push needle 31 and the implant 9 are protected before the implant 9 is delivered. During delivery, the puncture needle assembly 2 is required to retract to expose the push needle 31. The slide knob 24 is coupled with the puncture needle assembly 2, and the slide knob 24 enables the puncture needle assembly 2 to retract towards the proximal end by using a slide knob 24 provided on the housing 1.

The following provides an explanation in conjunction with the accompanying drawings and specific embodiments.

Embodiment 1

An intraocular implant delivery device as shown in FIGS. 1-19 includes a housing 1, a puncture needle assembly 2, a push needle assembly 3, a main control pull rod assembly 5, a slider assembly 6, a striking assembly 7, and a retracting needle turntable 8. A portion of the push needle assembly 3, a portion of the puncture needle assembly 2, the main control pull rod assembly 5, the slider assembly 6, the striking assembly 7, and the retracting needle turntable 8 are all arranged in the housing 1, and a button 4 and a slide knob 24 are provided on the housing 1.

Figure 1:
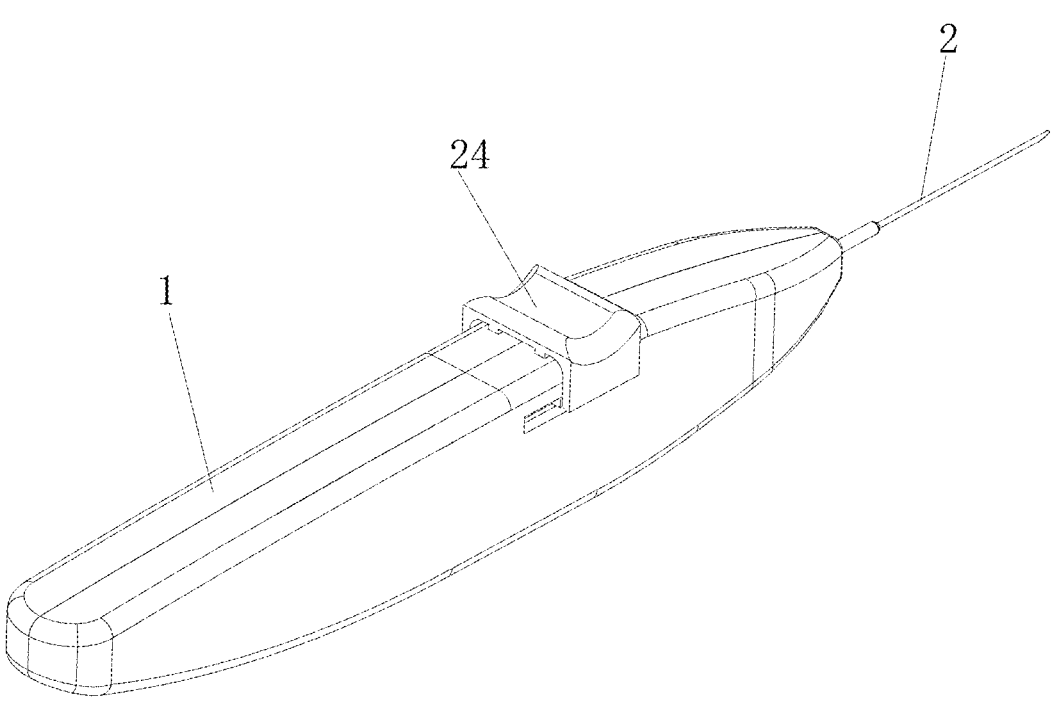
FIG. 1 is a schematic view of an overall structure of an intraocular implant delivery device in Embodiment 1 of the present application.
Figure 2:
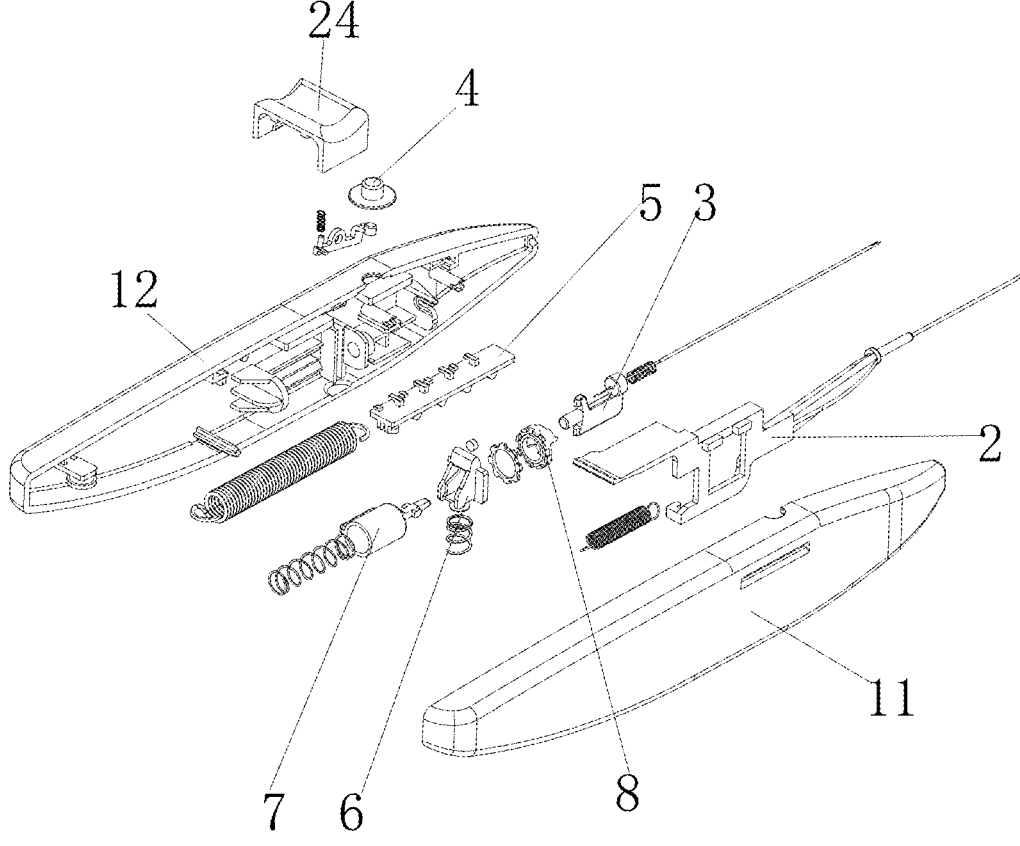
FIG. 2 is an exploded structural view of the intraocular implant delivery device in Embodiment 1 of the present application.

As shown in FIG. 1 and FIG. 2, the housing 1 includes a left housing 12 and a right housing 11. The left housing 12 and the right housing 11 are fixedly connected by snap connection, screw connection, adhesion or other fixed connection methods.

A through hole 13 is provided at a distal end of the housing 1, and a puncture needle 22 of the puncture needle assembly 2 passes through the through hole 13 and extends to an outer side of the housing 1. A push needle 31 of the push needle assembly 3 passes through an inner hole of the puncture needle 22 and extends to the outer side of the housing 1.

As shown in FIG. 3, several push needle guide limit members 121 are further provided inside the left housing 12. The push needle guide limit member 121 may be a support limit column, an axial limit groove is provided at a middle part of the support limit column, and a width of the limit groove is adapted to an outer diameter of the push needle. The push needle guide limit member 121 may alternatively be a guide limit plate provided with a limit groove, a width of which is adapted to an outer diameter of the push needle. The number of push needle guide limit members can be designed according to needs. For example, in the embodiments shown in the accompanying drawings, totally two support limit columns and one guide limit plate are provided, the guide limit plate is arranged between the two support limit columns, and the limit grooves on the support limit columns and the limit groove on the guide limit plate are on the same straight line, thereby ensuring that the push needle can only move straight axially and improving the implantation accuracy of the implant.

A chute 122 corresponding to a slider 61 of the slider assembly 6 is further provided inside the left housing 12, and the slider 61 is in sliding fit with the chute 122.

A retracting needle turntable assembly seat 123 is further provided inside the left housing 12, the retracting needle turntable assembly seat 123 includes an assembly plate and an assembly shaft, the assembly plate is fixedly connected to the housing 1, the assembly shaft is arranged on a distal side surface of the assembly plate, the assembly plate and the assembly shaft is each provided with a through hole at the middle part, and a striking head 71 of the striking assembly 7 and a striking portion 321 of the push needle assembly 3 pass through the through holes, so that the striking head 71 can smoothly strike the striking portion 321 of the push needle assembly 3.

A front guide limit plate 124 and a rear guide limit plate 125 for limiting the push needle assembly 3 are further provided inside the left housing 12. The front guide limit plate 124 and the rear guide limit plate 125 are arranged on a front side and a rear side of the push needle assembly seat 32 of the push needle assembly 3 respectively, so that the push needle assembly seat 32 can only move axially, thereby preventing the radial movement of the push needle 31 and improving the accuracy of implant implantation surgery.

As shown in FIG. 6 and FIG. 7, the main control pull rod assembly 5 includes a main control pull rod 51 and a spring, the spring may be a tension spring 23 with sufficient elasticity, a distal end of the tension spring 23 is fixedly connected to the main control pull rod, a right end of the tension spring is fixed to a spring fixing column inside the housing 1, the main control pull rod 51 is strip-shaped, a plurality of groups of first limit blocks 511 and second limit blocks 512 are provided on an upper side of the main control pull rod 51, and the first limit blocks 511 and the second limit blocks 512 are alternately arranged; the first limit blocks 511 are limit blocks arranged on the upper surface of the main control pull rod 51, the second limit block 512 includes a connecting portion and a limit portion, the limit portion is fixedly connected to the upper side of the main control pull rod 51 by the connecting portion and is arranged at a set distance from the upper side of the main control pull rod 51, a plurality of protrusions 513 are provided on a lower side of the main control pull rod 51, and a width of the protrusion 513 corresponds to a distance between the adjacent first limit blocks 511.

In the embodiment shown in FIG. 7, totally four protrusions 513 are provided on the lower side of the main control pull rod 51, and the protrusions 513 are approximately triangular. Correspondingly, four first limit blocks 511 and four second limit blocks 512 are provided on the upper side of the main control pull rod 51. The first limit blocks 511 and the second limit blocks 512 are alternately arranged from right to left on the upper side of the main control pull rod 51, and as shown in FIG. 7, the distance L between the adjacent first limit blocks 511 corresponds to the width D of the protrusion 513. Through this setting, at most four implants 9 can be delivered.

As shown in FIGS. 2, 6 and 8, the button 4 can actuate and limit the main control pull rod 51 through a lever 41 and a reset spring 42. The button 4 is arranged on the housing 1, a button port corresponding to the button 4 is provided on the housing 1, a shaft hole is provided at a middle part of the lever 41, a corresponding fixing shaft is provided inside the housing 1, the fixing shaft passes through the shaft hole on the lever 41, a distal end of the lever 41 corresponds to the button 4, a right end of the lever 41 is connected to the reset spring 42, and a positioning block 43 is provided on a right side of the lever 41. When the button is in a natural state, with the right end of the lever 41 under the action of the reset spring 42, and the positioning block 43 on the lever 41 limits the first limit blocks 511 on the main control pull rod 51. When the button 4 is pressed, the distal end of the lever 41 rotates downward, the right end of the lever 41 rotates upward, the positioning block 43 moves away from the first limit blocks 511 on the main control pull rod 51 and moves forward to a position corresponding to the second limit blocks 512, and the main control pull rod 51 moves axially towards a proximal end under the tension of the tension spring 23. When the second limit blocks 512 on the main control pull rod 51 move to the positioning block 43 on the lever 41, the positioning block 43 on the lever 41 re-limits the main control pull rod 51. When the button 4 is released, the lever 41 is reset under the action of the reset spring 42, the right end of the lever 41 rotates downward, the positioning block 43 moves away from the second limit blocks 512 on the main control pull rod 51, and the main control pull rod 51 continues to move towards the proximal end under the action of the tension spring 23. When the second one of the first limit blocks 511 moves to a side of the positioning block 43, the positioning block 43 re-limits the first limit blocks 511 on the main control pull rod 51.

As shown in FIG. 9 and FIG. 10, the slider assembly 6 is arranged below the main control pull rod 51, the slider assembly 6 includes a slider 61 and a compression spring 62, the slider 61 includes a side plate 611 and two guide plates 612 extending vertically outward from the side plate, the two guide plates 612 are spaced apart and are each provided with the guide curved surface 613, the through hole 614 corresponding to the striking assembly 7 is provided on the side plate 611 between the two guide plates 612, a spring positioning portion 615 is provided below the slider 61, the compression spring 62 is provided between the spring positioning portion 615 and the housing 1, and the driving member 63 is provided on one side of the through hole 614 of the side plate 611.

As shown in FIG. 11 and FIG. 12, the retracting needle turntable 8 is arranged on a distal side of the slider assembly 6, and the retracting needle turntable 8 is rotatably arranged inside the housing 1; several limit steps 81 are provided on a distal side surface of the retracting needle turntable 8, and the driving member 63 for driving the retracting needle turntable 8 to rotate is provided on the side plate 611 of the slider assembly 6; when the slider assembly 6 moves downward, the driving member 63 drives the retracting needle turntable 8 to rotate an angle corresponding to one step, so that the push needle 31 of the push needle assembly 3 moves one step towards the proximal end.

According to design requirements, the driving member 63 may adopt various implementation schemes. The retracting needle turntable 8 is provided with a component that interacts with the driving member 63. The interaction may be non-contact magnetic coupling or contact mechanical means. When the magnetic coupling is used, if the driving member 63 is a magnet, a component made of a magnetic material or a paramagnetic material with attractive force generated by the magnet is provided on the retracting needle turntable. If the driving member 63 is a component made of a magnetic material or a paramagnetic material with attractive force generated by a magnet, the magnet is provided on the retracting needle turntable 8.

In this embodiment, the driving member 63 may be a magnetic block 631. Correspondingly, an iron ring 82 is provided on the side of the retracting needle turntable 8 facing the side plate 611, and the iron ring 82 is embedded in the retracting needle turntable 8. When the slider assembly 6 moves downward, the magnetic block 631 attracts the iron ring 82 to generate an eccentric force to push the retracting needle turntable 8 to rotate an angle corresponding to one step, so that the push needle assembly 3 falls from a high step to a low step and moves axially towards the proximal end.

The limit steps 81 on the retracting needle turntable 8 are arranged in an arc direction of the retracting needle turntable 8. When the retracting needle turntable 8 rotates with the downward movement of the slider 61 and the slider 61 moves upward during resetting, the striking portion 321 of the push needle assembly 3 presses against the high step of the retracting needle turntable 8 to limit the retracting needle turntable 8 to rotate with the movement of the slider 61.

As shown in FIG. 13, the striking assembly 7 is arranged on a proximal side of the slider assembly 6, the striking assembly 7 includes a striking head 71 and a spring limit portion 72, a distal end of the spring presses against the spring limit portion 72 of the striking assembly 7, and a right end of the spring presses against the spring limit portion 72 inside the housing 1. In order to ensure that the striking assembly 7 can only move axially, the spring limit portion 72 is provided with a guide strip 721, a corresponding axial guide groove 126 is provided inside the housing 1, and the guide strip 721 is in sliding fit with the axial guide groove 126. The striking head 71 may be rod-like, and a left side and a right side of the striking head 71 are each provided with a guide limit block 711. When the slider assembly 6 slides downward, the guide limit blocks 711 slide along the guide curved surface 613 on the slider assembly 6, so that the striking head 71 moves towards a distal end to strike the push needle assembly 3. When the slider assembly 6 slides upward, the guide curved surface 613 on the slider assembly 6 pushes the striking head 71 to move towards a proximal end and the spring is compressed to store energy.

As shown in FIG. 14, the push needle assembly 3 includes a push needle 31, a push needle assembly seat 32 and a compression spring 33, a proximal end of the push needle assembly seat 32 is provided with a striking portion 321, two sides of the striking portion 321 of the push needle assembly seat 32 are each provided with a limit portion 322 that cooperate with the retracting needle turntable 8, and the push needle 31 is fixed on the push needle assembly seat 32. Because the push needle 31 is relatively long, several structures that fix the push needle 31 are further provided on the housing 1 to avoid shaking of the push needle and achieve precise axial movement.

A gear wall is further provided on the housing 1, and the compression spring 33 is sleeved on the push needle 31 and located between the push needle assembly seat 32 and the gear wall. In an initial state, the compression spring 33 is pre-compressed between the push needle assembly seat 32 and the gear wall, that is, the compression spring 33 is always compressed. The gear wall of the housing is immovable, and the compression spring 33 always provides a pressure towards the proximal end to press the push needle assembly seat 32 tightly on the retracting needle turntable 8. When the retracting needle turntable 8 rotates an angle of one step, the push needle assembly seat 32 retracts towards the proximal end under the action of the spring force, to move the elastic claw 36 at the distal end of the push needle 31 from the head 91 of the implant 9 to the tail 92 of the implant 9.

Specifically, in this embodiment, as shown in FIG. 15 and FIG. 16, the push needle 31 is a hollow needle, an implant positioning rod 34 is provided inside the push needle 31, the limit portions 322 are provided on the implant positioning rod 34, and the elastic claw 36 is provided at the distal end of the push needle 31. When the push needle 31 retracts, the elastic claw 36 opens when passing through the implant 9, so that the elastic claw 36 moves from the head 91 of the implant 9 on the implant positioning rod 34 to the tail 92 of the implant 9. When the striking head 71 of the striking assembly 7 strikes the push needle assembly 3, the push needle assembly 3 drives the push needle 31 to move towards the distal end of the housing 1, to push the implant 9 to the implantation site of the patient.

As shown in FIG. 17, the puncture needle assembly 2 includes a puncture needle assembly seat 21 and a puncture needle 22, the puncture needle assembly seat 21 is arranged in the housing 1, and the puncture needle 22 is fixedly connected to a distal end of the puncture needle assembly seat 21. The puncture needle assembly 2 further includes a tension spring 23 connected between a proximal end of the puncture needle assembly seat 21 and a tension spring fixing column inside the housing 1, a limit groove 211 is provided on the puncture needle assembly seat 21, a slide knob 24 corresponding to the limit groove 211 is provided on the housing 1, and the slide knob 24 is used for controlling the retraction of the puncture needle assembly 2. The slide knob 24 covers an outer surface of the button 4 to protect the button 4 and prevent accidental trigger of the button 4. The button 4 is exposed only when the slide knob 24 slides to enable the puncture needle assembly 2 to retract, and then the button 4 can be operated.

The puncture needle assembly seat 21 is arranged above the push needle assembly 3, and the push needle 31 passes through the inner hole of the puncture needle 22 and extends to the outer side of the housing 1. An elastic limit portion 212 is provided at a right end of the puncture needle assembly seat 21, a first limit rib 127 and a second limit rib 128 are provided on a right side of the elastic limit portion 212 inside the housing 1, and the second limit rib 128 is arranged on a right side of the first limit rib 127. The slide knob 24 can limit the puncture needle 22 axially.

With reference to FIG. 15 and FIG. 16 again, the intraocular implant delivered by the intraocular implant delivery device of the present application includes a disc-shaped tail 92, a cylindrical portion and a conical head 91, the cylindrical portion is arranged between the tail 92 and the head 91, the diameter of the head 91 gradually increases from an end of the head 91 to a connection position where the head 91 is connected with the cylindrical portion, and the diameter of the cylindrical portion is less than that of the head 91. The tail 92, the cylindrical portion, and the head 91 are each provided with an axial hole, a radial through hole is provided in the head 91, and the axial holes are in communication with the radial through hole.

The size of the intraocular implant in the embodiments of the present application is very small. For example, a commonly used intraocular implant has a length of 0.36 mm. Therefore, even a small precision difference may lead to the failure of ocular implantation surgery, and it is necessary to ensure the implantation precision of the intraocular implant delivery device.

A specific operation process of the intraocular implant delivery device during surgery in this embodiment is as follows.

Before leaving the factory, a required number of intraocular implants 9 are inserted into the implant positioning rod 34 and pushed to the limit portion 35 of the implant positioning rod 34. Then, the implant positioning rod 34 is inserted into the inner hole of the push needle 31. The elastic claw 36 at the distal end of the push needle 31 can limit the implants 9 to prevent the implants 9 from falling out. Next, the push needle assembly 3 is assembled into the inner hole of the puncture needle 22.

As shown in FIG. 18, in the initial state, the positioning block 43 on the lever 41 at the button 4 limits the first limit block 511 on the rightmost side of the main control pull rod 51. During surgery, the puncture needle 22 is first used to puncture the patient's eye tissue to form an incision. After the puncture is completed, the operator pushes the slide knob 24 to enable the puncture needle assembly 2 to retract away from the eye tissue.

As shown in FIG. 19, when the button 4 is pressed, the button 4 pushes the distal end of the lever 41 to rotate downward, the right end of the lever 41 rotates upward, the positioning block 43 on the lever 41 moves away from the first limit block 511 to release the limit on the main control pull rod 51, the main control pull rod 51 moves axially towards the proximal end under the action of the tension spring 23 until the second limit block 512 on the main control pull rod 51 moves to the position of the positioning block 43 on the lever 41, and then the main control pull rod 51 stops moving. During the movement of the main control pull rod 51, the protrusions 513 on the lower side of the main control pull rod 51 push the slider 61 of the slider assembly 6 to move downward. When the slider assembly 6 moves downward, the magnetic block 631 on the slider 61 attracts the iron ring 82 on the retracting needle turntable 8 to generate an eccentric force and drive the retracting needle turntable 8 to rotate an angle corresponding to one step, and the limit portion 322 on the push needle assembly 3 moves one step towards the proximal end along the steps. Meanwhile, when the compression spring 33 pushes the push needle 31 to move towards the proximal end, the elastic claw 36 at the distal end of the push needle 31 opens on an outer side of the implants 9, and the elastic claw 36 moves to the rear end of the tail 92 of the first implant 9. When the slider assembly 6 moves downward, the guide limit block 711 on the striking head 71 of the striking assembly 7 slides along the guide curved surface 613 of the slider. When the through hole 614 on the slider 61 is opposite to the striking head 71, the striking head 71 passes through the through hole 614 on the slider 61 and the through hole on the retracting needle turntable assembly seat 123, and strikes the striking portion 321 on the push needle assembly seat 32, to push the push needle 31 to move axially towards the distal end and push the implant 9 to reach the patient's trabecular meshwork site.

In the process of pressing the button 4, the main control pull rod assembly 5, the slider assembly 6, the retracting needle turntable 8, and the striking assembly 7 cooperate with each other to achieve retracting the push needle assembly 3, and when the elastic claw 36 retracts to the tail 92 of the next implant 9 to be struck, the striking head 71 is in place for striking.

After one implantation is completed, when the button 4 is released, the positioning block 43 on the lever 41 moves downward under the action of the reset spring 42 to release the limit on the second limit blocks 512 on the main control pull rod 51, and the main control pull rod 51 continues to move towards the proximal end under the action of the tension spring 23 until the positioning block 43 on the lever 41 limits the second one of the first limit blocks 511 on the main control pull rod 51. In this process, the valley position between the protrusions 513 on the lower side of the main control pull rod 51 moves to a position opposite to the slider 61, the slider 61 moves upward back to its initial position under the action of the compression spring 62, the guide limit block 711 on the striking head 71 of the striking assembly 7 slides along the guide curved surface 613 on the slider 61 and pushes the striking assembly 7 to move towards the proximal end, and the compression spring of the striking assembly 7 is compressed for the delivery of the next implant 9.

By repeating the above process, a plurality of intraocular implants 9 can be delivered to the patient's trabecular meshwork, so that the fluid in the anterior chamber of the patient's eye flows to Schlammer canals through the implants 9, to complete the delivery surgery of the intraocular implants.

Embodiment 2

On the basis of Embodiment 1, but unlike Embodiment 1, as shown in FIG. 20 and FIG. 21, the driving member 63 on the slider assembly 6 is an elastic plectrum 632 which is an elastic member, the elastic plectrum 632 is arranged on one side of the lateral through hole 614, several plectrum blocks 83 are provided on the side surface of the retracting needle turntable 8 close to the elastic plectrum 632, and the plectrum blocks 83 are distributed on the retracting needle turntable 8 at a set circumferential spacing. When the slider assembly 6 moves downward, the elastic plectrum 632 on the slider assembly 6 picks the plectrum blocks 83 to move, the retracting needle turntable 8 is driven to rotate an angle corresponding to one step, and the push needle 31 of the push needle assembly 3 moves one step along the axial proximal end.

The working principle of the intraocular implant delivery device in this embodiment is basically the same as that in Embodiment 1. Differences are as follows: when the slider assembly 6 moves downward, the elastic plectrum 632 on the slider assembly 6 can push the plectrum blocks 83 on the retracting needle turntable 8 to rotate an angle corresponding to one step, the push needle 31 of the push needle assembly

3 moves axially towards the proximal end by one step under the action of the compression spring 33, and the elastic claw 36 at the distal end of the push needle 31 opens and can move to the tail of the first implant 9; when the striking assembly 7 strikes the striking portion 321 of the push needle assembly 3, the push needle 31 can push the implant 9 into the surgical site of the patient, to complete one implantation of the implant 9; when the slider 61 moves upward, the push needle assembly does not move axially due to the blocking of high steps.

Embodiment 3

Compared with Embodiment 1, the intraocular implant delivery device in this embodiment has neither puncture needle assembly 2 nor slide knob 24. Other structures and the working principle are similar and will not be repeated here.

Although the embodiments of the present application are shown and described, it will be understood by those of ordinary skill in the art that various changes, modifications, substitutions, and variations can be made to these embodiments without departing from the principles and spirit of the present application. The scope of the present application is defined by the appended claims and equivalents thereof.

What is claimed is:

1. An intraocular implant delivery device, comprising a housing, a main control pull rod assembly, a slider assembly, a striking assembly, a retracting needle turntable, and a push needle assembly, the main control pull rod assembly, the slider assembly, the striking assembly, and the retracting needle turntable being arranged in the housing, a through hole being provided at a distal end of the housing, a push needle of the push needle assembly extending through the through hole to an outer side of the housing, and the main control pull rod assembly, the slider assembly, and the striking assembly being each provided with an energy source capable of selectively releasing energy, wherein the main control pull rod assembly is actuated by an operator through a button arranged on the housing to enable the energy source to drive the main control pull rod assembly to move in an axial direction;

wherein the main control pull rod assembly comprises a main control pull rod and a first spring, the slider assembly is adjacent to the main control pull rod in a longitudinal direction, and a plurality of protrusions are provided on a side surface of the main control pull rod facing the slider assembly; when the button is pressed and the main control pull rod moves axially, the protrusions is configured to push the slider assembly to move away from the button in the longitudinal direction; when the protrusions move away from the slider assembly with the main control pull rod, the energy source pushes the slider assembly to move close to the button to an initial position in the longitudinal direction;

wherein the retracting needle turntable is arranged on a distal side of the slider assembly, a plurality of limit steps are provided on a side surface of the retracting needle turntable facing the push needle assembly, and a driving member for driving the retracting needle turntable to rotate is provided on the slider assembly; when the slider assembly moves away from the button in the longitudinal direction, the driving member drives the retracting needle turntable to rotate an angle corresponding to one step to enable the push needle of the push needle assembly to retract one step towards a proximal end;

wherein the striking assembly is arranged on a side of a proximal end of the slider assembly, when the slider assembly is in an initial position, the energy source connected to the striking assembly is in an energy storage state, and when the slider assembly moves away from the button in the longitudinal direction, the striking assembly moves along a guide curved surface of the slider assembly towards the distal end under the push of the energy source to strike the push needle assembly; and wherein the push needle assembly is arranged on a side of a distal end of the retracting needle turntable, at least one implant is accommodated inside the push needle, and an elastic claw is provided at a distal end of the push needle; when the push needle restricts towards the proximal end, the elastic claw opens when passing by the implant to enable the elastic claw to move from a head of the implant to a tail of the implant, and when the striking assembly strikes the push needle assembly, the push needle assembly drives the push needle to move towards a distal end of the housing, to push the implant to an implantation site of a patient.

2. The intraocular implant delivery device according to claim 1, wherein the energy source is a spring, motor, magnetic iron, or elastomer.

3. The intraocular implant delivery device according to claim 1, wherein the first spring is the energy source connected to the main control pull rod, one end of the first spring is fixed to the main control pull rod and the other end of the first spring is fixed to the housing;

wherein when the button is in the initial position, the button limits the main control pull rod, and the first spring is in the energy storage state, and when the button is pressed, the spring pushes the main control pull rod to move towards the proximal or distal end in the axial direction.

4. The intraocular implant delivery device according to claim 3, wherein a plurality of groups of first limit blocks and second limit blocks are provided on a side surface of the main control pull rod away from the slider assembly, and the first limit blocks and the second limit blocks are alternately arranged to limit the main control pull rod when the button is pressed and released; and a width of the protrusion corresponds to a distance between the adjacent first limit blocks.

5. The intraocular implant delivery device according to claim 1, wherein the button actuates the main control pull rod through a lever and a reset spring, a shaft hole being provided at a middle part of the lever, a fixing shaft being provided inside the housing, the fixing shaft passing through the shaft hole in the lever, one end of the lever corresponding to a position of the button, the other end of the lever being connected to the reset spring, and a positioning block being provided on the lever to limit the main control pull rod.

6. The intraocular implant delivery device according to claim 1, wherein the slider assembly comprises a slider and a second spring connected to the slider, which comprises a side plate, two guide plates extending vertically outward from the side plate and spaced apart, opposite surfaces of the two guide plates being each provided with the guide curved surface, the through hole corresponding to the striking assembly being provided in the side plate between the two guide plates, and the driving member being arranged on the side plate of the slider.

7. The intraocular implant delivery device according to claim 6, wherein a component magnetically coupled with the driving member is provided on the retracting needle turntable; when the slider assembly moves away from the button in the longitudinal direction, the driving member pushes the retracting needle turntable to rotate an angle corresponding to one step under the action of magnetic force, so that the push needle of the push needle assembly retracts one step axially towards the proximal end in the axial direction.

8. The intraocular implant delivery device according to claim 6, wherein the driving member is an elastic plectrum, several plectrum blocks are provided on the retracting needle turntable, and the plectrum blocks are distributed on the retracting needle turntable at a set circumferential spacing; when the slider assembly moves away from the button in the longitudinal direction, the elastic plectrum on the slider assembly pushes the plectrum blocks to move, the retracting needle turntable is driven to rotate an angle corresponding to one step, and the push needle of the push needle assembly retracts one step towards the proximal end in the axial direction.

9. The intraocular implant delivery device according to claim 1, wherein the striking assembly comprises a striking head and a spring limit portion, a third spring is provided between the spring limit portion and the housing, and a guide limit block is provided on the striking head; when the slider assembly slides away from the button in the longitudinal direction, the guide limit block slides along the guide curved surface, so that the striking head moves towards the distal end to strike the push needle assembly; when the slider assembly slides close to the button in the longitudinal direction, the guide curved surface pushes the striking head to move towards the proximal end, and the third spring stores energy.

10. The intraocular implant delivery device according to claim 9, wherein a guide strip is provided at a lower part of the spring limit portion, a corresponding axial guide groove is provided inside the housing, and the guide strip is in sliding fit with the axial guide groove.

11. The intraocular implant delivery device according to claim 1, wherein the push needle assembly comprises the push needle, a push needle assembly seat, and a compression spring; the push needle is fixed on the push needle assembly seat, a gear wall is provided on the housing, the compression spring is sleeved on the push needle and connected between the push needle assembly seat and the gear wall, and the push needle assembly seat abuts against the steps of the retracting needle turntable, so that when the retracting needle turntable rotates, the compression spring pushes the push needle assembly seat to move towards the proximal end the axial direction, to drive the push needle to move from the head of the implant to the tail of the implant; the striking assembly strikes the push needle assembly seat when moving towards the distal end, to push the push needle to strike the implant.

12. The intraocular implant delivery device according to claim 1, further comprising a puncture needle assembly for forming an incision in an ocular tissue, wherein a slide knob is further provided on the housing to control the puncture needle assembly to retract towards the proximal end.

* * * * *